United States Patent
Tournilhac et al.

(12)

(10) Patent No.: US 6,287,552 B1
(45) Date of Patent: Sep. 11, 2001

(54) COSMETIC OR DERMATOLOGICAL TOPICAL COMPOSITIONS COMPRISING DENDRITIC POLYESTERS

(75) Inventors: Florence Tournilhac, Paris; Pascal Simon, Vitry sur Seine, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/397,517

(22) Filed: Sep. 17, 1999

(30) Foreign Application Priority Data

Sep. 17, 1998 (FR) .................................................. 98 11634

(51) Int. Cl.[7] .......................... A61K 31/74; C08F 20/00; C08G 63/78; C08G 63/00; C08G 63/48

(52) U.S. Cl. ................ 424/78.03; 424/401; 424/70.1; 424/60; 424/61; 424/62; 424/63; 424/70.11; 424/78.02; 424/78.03; 424/78.17; 424/78.08; 424/DIG. 2; 424/DIG. 3; 424/DIG. 16; 514/788.1; 514/844; 514/845; 514/846; 514/847; 514/848; 514/858; 514/859; 514/860; 514/861; 514/862; 514/863; 514/864; 514/865; 514/881; 514/887; 514/937; 514/944; 514/945; 514/772.1; 514/784; 523/122; 525/437; 525/444; 525/444.5; 525/445; 525/450; 525/242; 528/271; 528/274; 528/295.5

(58) Field of Search .................................. 424/78.03, 400, 424/401, 70.1, 63, 62, 64, 60, 70.11, 78.02, 78.08, 78.17, DIG. 2, DIG. 3, DIG. 16; 514/788.1, 844–848, 858–865, 881, 887, 937, 944, 945, 772.1, 784; 523/122; 525/437, 444, 444.5, 445, 450, 242; 528/271, 274, 295.5

(56) References Cited

U.S. PATENT DOCUMENTS 5,530,092 * 6/1996 Meijer et al. ......................... 528/363
6,001,367 * 12/1999 Bazin et al. ....................... 424/195.1

FOREIGN PATENT DOCUMENTS

WO 93/17060  9/1993 (WO).

OTHER PUBLICATIONS

Grant & Hackh's Chemical Dictionary, Roger Grant & Claire Grant, 5th Ed., McGraw–Hill Book Company, 1987, p294.*

* cited by examiner

*Primary Examiner*—Diana Dudash
*Assistant Examiner*—Jean-Michel Campagne
(74) *Attorney, Agent, or Firm*—Oblon, Spivak, McClelland, Maier & Neustadt, P.C.

(57) ABSTRACT

The present invention relates to cosmetic or dermatological compositions capable of being applied to the skin, the keratinous fibers, the nails, the semimucous membranes and/or the mucous membranes, and which includes a dendritic polyester polymer having terminal hydroxyl functional groups or the combination of such a polymer with a film-forming polymer. It also relates to methods of cosmetic or dermatological treatment using these compositions as well as the use of the compositions for the preparation of dermatological or cosmetic compositions.

22 Claims, No Drawings

COSMETIC OR DERMATOLOGICAL TOPICAL COMPOSITIONS COMPRISING DENDRITIC POLYESTERS

BACKGROUND OF THE INVENTION

1. Field of the Invention

The present invention relates to the use, in cosmetic or dermatological topical compositions, of a dendritic polyester polymer and/or of the combination of the dendritic polymer with a film-forming polymer, and the topical cosmetic or dermatological compositions containing these polymers.

2. Discussion of the Background

In cosmetology and dermatology, it is advantageous to have compositions which are capable of forming films when they are applied to the skin. Compositions having film-forming properties have the advantages of, for example, promoting the evenness of applied layers, reinforcing skin-softening and protecting action, improving the quality of the deposition of make-up products such as foundations and lipsticks, and imparting transfer-resistance (so-called "transfer-free" products), or alternatively, in the case of packs or cataplasms, facilitating cleansing of the skin simply by peeling off the dried composition.

The components imparting the above-noted film-forming properties are generally high-molecular-weight polymers. To obtain substantial film-forming properties in cosmetic or dermatological compositions, it is not satisfactory to simply increase the concentration of these high-molecular-weight polymers in the cosmetic or dermatological compositions. Such an approach is indeed limited by the fact that these polymers excessively increase the viscosity of the finished product. The finished product becomes too thick; it is thus difficult to apply to the skin and therefore loses its sensory qualities.

The present inventors have now discovered that it is possible to overcome the above-noted disadvantages, i.e. to reinforce the film-forming properties of topical cosmetic or dermatological compositions without damaging their sensory properties, by using a new type of polymer called a dendritic polymer or dendrimer having a polyester structure with terminal hydroxyl groups.

Indeed, these dendritic polymers or dendrimers described in greater detail below, although only very slightly viscous, have now been found particularly capable of reinforcing the cohesion of a film formed by customary film-forming polymers. Their incorporation into topical cosmetic or dermatological formulations has no damaging effects on their texture or sensory properties.

SUMMARY OF THE INVENTION

The subject of the present invention therefore relates to a topical cosmetic or dermatological composition, which can be applied to the skin, the keratinous fibres, the nails, the semimucous membranes and/or the mucous membranes, that includes a dendritic polyester polymer having terminal hydroxyl functional groups, or includes the combination of a dendritic polyester polymer having terminal hydroxyl functional groups with a film-forming polymer.

The subject of the present invention also relates to a method of cosmetic treatment using a cosmetic composition that includes a dendritic polyester polymer having terminal hydroxyl functional groups, or includes the combination of a dendritic polyester polymer having terminal hydroxyl functional groups with a film-forming polymer.

The subject of the present invention also relates to the use of a composition including a dendritic polyester polymer having terminal hydroxyl functional groups, or including the combination of a dendritic polyester polymer having terminal hydroxyl functional groups with a film-forming polymer, for the preparation of a dermatological composition intended for the treatment of the skin.

Accordingly, one embodiment of the invention provides a topical cosmetic or dermatological composition, which may be applied to the skin, the keratinous fibres, the nails, the semimucous membranes and/or the mucous membranes, that includes, in a physiologically acceptable medium, a dendritic polyester polymer having terminal hydroxyl functional groups.

Another embodiment of the invention provides a topical cosmetic or dermatological composition, which may be applied to the skin, the keratinous fibres, the nails, the semimucous membranes and/or the mucous membranes, that includes, in a physiologically acceptable medium:

(A) a dendritic polyester polymer having terminal hydroxyl functional groups; and (B) at least one film-forming polymer.

Another embodiment of the invention provides a method of treatment, that includes applying the above composition to the skin, the nails, the keratinous fibres, the semimucous membranes and/or the mucous membranes.

Another embodiment of the invention provides a method of treatment, that includes spreading the above composition to a part to be treated in a thickness allowing the formation of a film, leaving the composition in contact with the part for a sufficient period to obtain the desired cosmetic or dermatological effect and to allow the partial or complete drying of the composition and removing the film thus formed by peeling off at the end of the period.

DESCRIPTION OF THE PREFERRED EMBODIMENTS

Other features and attendant advantages of the present invention will be more fully appreciated as the same becomes better understood from the following detailed description, which is not intended to be limiting unless otherwise specified.

The compositions according to the invention find a particularly advantageous application in the field of the care of the skin and/or the application of make-up to the skin of the face and of the body, the keratinous fibres, the nails, the mucous membranes and/or the semimucous membranes. Preferably, mucous membrane is understood to mean the internal part of the lower eyelid; semimucous membrane is understood to mean the lips of the face and keratinous fibres are understood to mean in particular the eyelashes, the eyebrows and the hair.

The compositions according to the invention containing the combination of a dendrimer and of a film-forming polymer are in particular very effective when they are used as peelable packs (so-called "Peel Off" packs. These include gels, preferably based on poly(vinyl alcohol), which are spread in a thick layer on the skin of the face or of the body and are removed simply by peeling off the dried film. The film-forming power of the film-forming polymer-dendrimer combination then ensures good cohesion of the film which is removed in a single piece and does not leave small fragments to be subsequently removed.

The dendritic polymers or dendrimers (from the Greek dendron=tree) are "arborescent", that is to say highly branched, polymer molecules invented by D. A. Tomalia and his team at the beginning of the 1990's (Donald A. Tomalia et al., *Angewandte Chemie, Int. Engl. Ed.*, Vol. 29, No. 2, pages 138–175, the entire contents of which are hereby incorporated by reference). They are molecular structures constructed around a generally polyvalent central unit. Branched units for chain-extension are linked around this central unit, in concentric layers and according to a perfectly defined structure, thus giving rise to monodispersed symmetric macromolecules having a well-defined chemical and stereochemical structure.

The dendritic polymers used in the cosmetic or dermatological compositions of the present invention are dendrimers having the chemical structure of a polyester and which end with hydroxyl groups. The structure and the preparation of these polymers is described in Patent Applications WO-A-93/17060 and WO-96/12754, the entire contents of each of which being hereby incorporated by reference.

More preferably, the dendritic polymers used in the compositions of the present invention may be defined as being highly branched macromolecules of the polyester type, that include:

a central unit derived from an initiator compound carrying one or more hydroxyl functions (a), chain-extension units derived from a chain-extension molecule carrying a carboxyl function (b) and at least two hydroxyl functions (c), each of the hydroxyl functions (a) of the central molecule being the starting point of a polycondensation reaction (by esterification) which starts with the reaction of the hydroxyl functions (a) of the central molecule with the carboxyl functions (b) of the chain-extension molecules, and then continues with the reaction of the carboxyl functions (b) with the hydroxyl functions (c) of the chain-extension molecules.

The initiator compound carrying one or more hydroxyl functions and forming the central unit around which the dendritic structure will be constructed is preferably a mono-, di- or polyhydroxylated compound. It may be chosen from:

(a) a monofunctional alcohol,
(b) an aliphatic, cycloaliphatic or aromatic diol,
(c) a triol,
(d) a tetrol,
(e) a sugar alcohol,
(f) anhydro-ennea-heptitol or dipentaerythritol,
(g) an a-alkylglycoside,
(h) a polyalkoxylated polymer obtained by polyalkoxylation of one of the alcohols (a) to (g), having a molar mass at most equal to 8000.

Preferred initiator compounds serving for the preparation of the dendritic polyesters used in the present invention include ditrimethylolpropane, ditrimethylolethane, dipentaerythritol, pentaerytliritol, an alkoxylated pentaerythritol, trimethyloletliane, trimethylolpropane, an alkoxylated trimethylolpropane, glycerol, neopentyl glycol, dimethylolpropane or 1,3-dioxane-5,5-dimethanol.

Preferably, the hydroxylated initiator compounds which may form the central unit of the future dendrimer are reacted with molecules called chain-extension molecules which are diol-monoacid-type compounds preferably chosen from:

monocarboxylic acids containing at least two hydroxyl functions, and monocarboxylic acids containing at least two hydroxyl functions of which one or more carry a hydroxyalkyl substituent.

Preferred examples of such compounds are dimethylolpropionic acid,

α,α-bis(hydroxymethyl)butyric acid, α,α,α-tris(hydroxymethyl)acetic acid,

α,α-bis(hydroxymethyl)valeric acid, α,α-bis(hydroxy)propionic acid and 3,5-dihydroxybenzoic acid.

In a particularly preferred embodiment of the present invention, the initiator compound is chosen from ditrimethylolpropane, trimethylolpropane, an ethoxylated pentaerythritol, pentaerythritol or glycerol, and the chain-extension molecule is dimethylolpropionic acid.

The dendritic polymers of the polyester type with terminal hydroxyl functions which are used in the compositions of the present invention are preferably characterized in that some of the terminal hydroxyl functions of the polyester-type dendritic polymer may carry substituents derived from at least one chain-terminating agent.

A polymer without derived substituents is preferably used. However, when some of the terminal hydroxyl functions carry a derived substituent, the fraction of these terminal hydroxyl functions carrying a chain-terminating unit is preferably between 1 and 90 mol %, more preferably between 10 and 50 mol % relative to the total number of terminal hydroxyl functions.

The chain-terminating agent is preferably chosen so as to make it possible to modify at will the physicochemical properties of the dendritic polyesters used in the compositions of the present invention.

The chain-terminating agent may be chosen from a wide variety of compounds capable of forming covalent bonds with the terminal hydroxyl functions. These compounds preferably include:

i) a saturated monocarboxylic acid or a saturated fatty acid or an anhydride of such a compound, ii) an unsaturated fatty acid, iii) an unsaturated monocarboxylic acid, iv) a diisocyanate or an oligomer of such a compound, v) an addition product prepared from a compound according to iv), vi) a dicarboxylic or polycarboxylic acid or an anhAydride of such a compound, vii) an addition product prepared from a compound according to vi), viii) an aromatic monocarboxylic acid, ix) an epihalohydrin, x) a glycidyl ester of a monocarboxylic acid or of a fatty acid containing from 1 to 24 carbon atoms, xi) an epoxide of an unsaturated fatty acid containing from 3 to 24 carbon atoms.

Preferred chain-terminating compounds include lauric acid, linseed fatty acids, soyabean fatty acids, tallow fatty acids, dehydrogenated castor oil fatty acids, caproic acid, caprylic acid, diallyl ether maleate of trimethylolpropane, methacrylic acid and acrylic acid.

Particularly preferred dendritic polymers of the polyester type with terminal hydroxyl functions and optionally carrying chain-terminating groups are known and are marketed by the company PERSTORP.

Particularly preferred polymers used in the present invention include:

a dendritic polyester obtained by polycondensation of dimethylolpropionic acid with trimethylolpropane, free of chain-terminating agents, marketed under the name BOLTORN H40 TMP CORE;

a dendritic polyester obtained by polycondensation of dimethylolpropionic acid with polyoxyethylenated pentaerythritol (5 EO units on each hydroxyl function), in which 50% of the hydroxyl functions are esterified with capric/caprylic acid (technical name esterified HBP 3G);

a dendritic polyester obtained by polycondensation of dimethylolpropionic acid with polyoxyetlhyleniated pentaerythritol (5 EO units on each hydroxyl function), free of chain-terminating agent (technical name HBP Polyol 3G), all these polymers being products from the company PERSTORP.

In the compositions of the present invention, the dendritic polymers of the polyester type with terminal hydroxyl groups may be combined with film-forming polymers with the aim of reinforcing their film-forming power. For that, it is possible to use a variety of known and physiologically acceptable film-forming polymers.

Preferred film-forming polymers which can be used in the present invention include synthetic polymers obtained by polycondensation or free-radical polymerization, polymers of natural origin and mixtures thereof.

There may be mentioned, for example, the anionic, cationic, nonionic or amphoteric polyurethanes, acrylic polyurethanes, copolymers of the polyurethane-polyvinylpyrrolidone type, poly(urethane esters), poly(urethane ethers), polyureas, poly(urethane ureas), polyesters, poly(amide esters), polyesters with fatty chain(s), polyamides, epoxy ester resins, acrylic and/or vinyl polymers and/or copolymers, acrylic/silicone copolymers, nitrocellulose/acrylic copolymers, optionally modified polymers of natural origin, polymers resulting from the free radical polymerization of one or more monomers inside and/or partially at the surface of pre existing particles of at least one polymer chosen from the group formed by polyurethanes, polyureas, polyesters, poly(amide esters) and/or alkyds and mixtures of these polymers.

In a preferred embodiment of the invention, the film-forming polymer is poly(vinyl acetate) optionally partially or completely hydrolysed and in particular poly(vinyl alcohol), in other words a poly(vinyl acetate) more than 80% hydrolysed. Such a preferred poly(vinyl alcohol) is marketed, for example, by the company AIR PRODUCTS under the name AIRVOL 540 (88% hydroxylated).

In the topical cosmetic or dermatological compositions of the present invention containing dendrimers combined with film-forming polymers, the weight ratio of the dendritic polymer to the film-forming polymer is preferably within the interval ranging from 1/100 to 1/1, and more preferably within the interval ranging from 1/15 to 1/1.

The dendritic polymer is present in the compositions of the present invention in a preferred amount of 0.1 to 5% by weight and more preferably in an amount of 0.5 to 2% by weight relative to the total composition.

The topical compositions according to the invention may contain, in addition, one or more cosmetic or dermatological active ingredients, or alternatively one or more physiologically acceptable solvent or adjuvants customarily used in cosmetics or dermatology.

The cosmetic or pharmaceutical active ingredients include, for example, anti-inflammatory agents, antibacterials, antifungals, antivirals, antiseboithocic agents, anti-acne agents, keratolytics, antihistamines, anaesthetics, cicatrizing agents, pigmentation modifiers, sunscreens, anti-free radical agents, moisturizing agents, vitamins, proteins, ceramides and other similar compounds.

The solvents which the cosmetic or dermatological compositions of the invention may contain are preferably chosen from water, lower monoalcohols such as ethanol or isopropanol, glycols such as diethylene glycol, glycol ethers such as alkyl ethers of ethylene glycol or of diethylene glycol, or fatty acid esters, these solvents being used alone or in the form of a mixture.

The physiologically acceptable adjuvants are chosen from pH-regulating agents, antioxidants, preservatives, pigments and colourings, emollients, antifoams, plant or animal oils or waxes, silicones, perfumes, surfactants, plasticizers, thickening polymers other than those of the invention and other similar compounds.

Of course, persons skilled in the art will be careful to choose this or these optional additional compounds and their quantity so that the advantageous properties intrinsically attached to the cosmetic or dermatological composition in accordance with the invention are not, or not substantially, altered by the addition(s) envisaged.

The cosmetic or dermatological compositions of the present invention may be provided in a fluid, gelled, semi-solid or even solid form, for example in the form of oil-in-water or water-in-oil emulsions, of aqueous or aqueous-alcoholic gels.

The compositions of the present invention may find particular application as skin care or protection products, make-up products such as foundations, lipsticks, blushers or eyeshadows, mascaras, eyeliners, nail varnish, or formulations for "peel off" packs.

A preferred form of presentation of a composition according to the invention is a formulation for "peel off" packs containing the combination of a poly(vinyl alcohol) and of a dendrimer of the polyester type with terminal hydroxyl groups.

Another preferred embodiment of the present invention relates to a method of cosmetic treatment that includes, for example:

applying, and optionally bringing about the penetration of, a topical cosmetic composition according to the invention to the skin, the nails, the keratinous fibres, the semimucous membranes and/or the mucous membranes, or spreading the cosmetic composition according to the present invention on the part to be treated in a thickness allowing the formation of a film, leaving the composition in contact with the skin for a sufficient period to obtain the desired cosmetic effect and to allow the partial or complete drying of the composition and in removing the film thus formed simply by peeling off at the end of this exposure time.

EXAMPLES

Having generally described this invention, a further understanding can be obtained by reference to certain specific examples, which are provided herein for purposes of illustration only and are not intended to be limiting unless otherwise specified.

Example 1

Three compositions for "peel off" packs are prepared in which two (compositions A and B), in accordance with the present invention, contain the combination of poly(vinyl alcohol) and a dendrimer, and a third (composition C), corresponding to the state of the art, contains poly(vinyl alcohol) as sole film-forming component.

The table below groups together the constituents of these three compositions as well as the sensory evaluations relating to the removal of a film applied to a glass plate by peeling off after drying.

| Composition | A | B | C (comparative) |
|---|---|---|---|
| poly(vinyl alcohol)* | 9.75 | 9.75 | 9.75 |
| dendritic polyester* | 1 | 1 | 0 |
| water | 79.12 | 78 | 77.87 |
| ethanol | 10 | 10 | 10 |
| plasticizer (PEG 75) | 0 | 1.13 | 2.25 |
| preservative | 0.13 | 0.13 | 0.13 |
| | very rigid film, easy to remove | flexible and rigid film, very easy to remove | flexible, not very rigid film, very difficult to remove |

*the poly(vinyl alcohol) is the product AIRVOL 540 marketed by the company AIR PRODUCTS and the dendritic polyester is the dendrimer of trimethylolpropane and of dimethylolpropionic acid with terminal hydroxyl groups marketed by the company PERSTORP under the name BOLTORN H40 TMP CORE.

It is observed that the presence of the dendritic polymer reinforces the cohesion of the dried film and very markedly facilitates its removal by peeling off.

Example 2
"Peel Off" Pack:

A formulation for "peel off" packs is prepared by mixing the following components in the quantities indicated:

| | |
|---|---|
| poly(vinyl alcohol)* | 10 g |
| dendritic polyester* | 1 g |
| ethanol | 10 g |
| PEG 75 | 1 g |
| glycerol | 2 g |
| active ingredient (fruit acids) | 1 g |
| perfume | 0.4 g |
| preservatives | 0.3 g |
| deionized water qs | 100 g |

*the poly(vinyl alcohol) and the dendritic polyester are those used in Example 1.

Example 3
Film-forming Care Cream:

A care cream is prepared from the following ingredients:

| | |
|---|---|
| poly(vinyl alcohol)* | 1.5 g |
| dendritic polyester* | 0.25 g |
| ethanol | 2 g |
| PEG 40 stearate | 1.2 g |
| glycerol | 3 g |
| glyceryl stearate | 1 g |
| cetyl alcohol | 2 g |
| cyclomethicone (D₅) | 5 g |
| karite oil | 5 g |
| active ingredient (tocopherol) | 1 g |
| perfumes | 0.4 g |
| preservatives | 0.3 g |
| deionized water qs | 100 g |

*the poly(vinyl alcohol) and the dendritic polyester are those used in Example 1.

Having now fully described this invention, it will be apparent to one of ordinary skill in the art that many changes and modifications can be made thereto without departing from the spirit or scope of the invention as set forth herein.

This application is based on FR 98 11634, filed Sep. 17, 1998, the entire contents of which are hereby incorporated by reference.

What is claimed is:

1. A topical cosmetic or dermatological composition, which may be applied to the skin, the keratinous fibres, the nails, the semimucous membranes and/or the mucous membranes, comprising, in a physiologically acceptable medium, a dendritic polyester polymer having terminal hydroxyl functional groups.

2. The composition according to claim 1, wherein the dendritic polyester polymer having terminal hydroxyl functional groups is a highly branched macromolecule, comprising:

a central molecule derived from an initiator compound carrying one or more hydroxyl functions (a), chain-extension units derived from a chain-extension molecule carrying a carboxyl function (b) and at least two hydroxyl functions (c), wherein each of the hydroxyl functions (a) of the central molecule are the starting point of a polycondensation reaction (polyesterification) which starts with the reaction of the hydroxyl functions (a) of the central molecule with the carboxyl functions (b) of the chain-extension molecules, and then continues with the reaction of the carboxyl functions (b) with the hydroxyl functions (c) of the chain-extension molecules.

3. The composition according to claim 2, wherein the initiator compound is selected from the group consisting of:

(a) a monofunctional alcohol, (b) an aliphatic, cycloaliphatic or aromatic diol, (c) a triol, (d) a tetrol, (e) a sugar alcohol, (f) anhydro-ennea-heptitol or dipentaerythritol, (g) an α-alkylglycoside, and (h) a polyalkoxylated polymer obtained by polyalkoxylation of one of the alcohols (a) to (g), having a molar mass at most equal to 8000.

4. The composition according to claim 2, wherein the initiator compound is selected from the group consisting of ditrimethylolpropane, ditrimethylolethane, dipentaerythritol, pentaerythritol, an alkoxylated pentaerytlritol, trimethylolethane, trimethylolpropane, an alkoxylated trimethylolpropane, glycerol, neopentyl glycol, dimethylolpropane and 1,3-dioxane-5,5-dimethanol.

5. The composition according to claim 2, wherein the chain-extension molecule is selected from the group consisting of:

monocarboxylic acids containing at least two hydroxyl functions, and monocarboxylic acids containing at least two hydroxyl functions of which one or more carry a hydroxyalkyl substituent.

6. The composition according to claim 2, wherein the chain-extension molecule is selected from the group consisting of dimethylolpropionic acid, α,α-bis(hydroxymethyl)butyric acid, α,α,α-tris(hydroxymethyl)acetic acid, α,α-bis(hydroxymethyl)valeric acid, α,α-bis(hydroxy)propionic acid and 3,5-dihydroxybenzoic acid.

7. The composition according to claim 2, wherein the initiator compound is selected from the group consisting of ditrimethylolpropane, trimethylolpropane, an ethoxylated pentaerythritol, pentaerythritol or glycerol, and wherein the chain-extension molecule is dimethylolpropionic acid.

8. The composition according to claim 1, wherein at least one of the terminal hydroxyl functional groups comprise at least one substituent derived from at least one chain-terminating agent.

9. A topical cosmetic or dermatological composition, which may be applied to the skin, the keratinous fibres, the nails, the semimucous membranes and/or the mucous membranes, comprising, in a physiologically acceptable medium:
  (A) a dendritic polyester polymer having terminal hydroxyl functional groups; and
  (B) at least one film-forming polymer.

10. The composition according to claim 9, wherein the film-forming polymer is a physiologically acceptable film-forming polymer selected from the group consisting of anionic, cationic, nonionic or amphoteric polyurethanes, acrylic polyurethanes, polyurethane-polyvinylpyrrolidone copolymers, poly(urethane esters), poly(urethane ethers), polyureas, poly(urethane ureas), polyesters, poly(amide esters), polyesters with fatty chain(s), polyamides, epoxy ester resins, acrylic and/or vinyl polymers and/or copolymers, acrylic/silicone copolymers, nitrocellulose/acrylic copolymers, optionally modified polymers of natural origin, and polymers resulting from the free-radical polymerization of one or more monomers inside and/or partially at the surface of pre-existing particles of at least one polymer selected from the group consisting of polyurethanes, polyureas, polyesters, poly(amide esters) and/or alkyds and mixtures thereof, and mixtures thereof.

11. The composition according to claim 9, wherein the film-forming polymer is a poly(vinyl acetate) optionally partially hydrolysed to poly(vinyl alcohol).

12. The composition according to claim 9, wherein the film-forming polymer is poly(vinyl alcohol).

13. The composition according to claim 9, wherein the weight ratio of the dendritic polymer to the film-forming polymer is within the interval ranging from 1/100 to 1/1.

14. The composition according to claim 9, wherein the concentration of the dendritic polymer relative to the total composition is 0.1 to 5% by weight.

15. The composition according to claim 9, further comprising one or more cosmetic or pharmaceutical active ingredient(s) customarily used in topical application.

16. The composition according to claim 15, wherein the active ingredient(s) are selected from the group consisting of anti-inflammatory agents, antibacterials, antifungals, antivirals, antiseborrhoeic agents, anti-acne agents, keratolytics, antihistamines, anaesthetics, cicatrizing agents, pigmentation modifiers, sunscreens, anti-free radical agents, moisturizing agents, vitamins, proteins, ceramides and mixtures thereof.

17. The composition according to claim 9, further comprising one or more solvents or adjuvants selected from the group consisting of water, lower monoalcohols, ethanol or isopropanol, glycols, diethylene glycol, glycol ethers, alkyl ethers of ethylene glycol or of diethylene glycol, fatty acid esters, pH-regulating agents, antioxidants, preservatives, pigments, colourings, emollients, antifoams, plant or animal oils or waxes, silicones, perfumes, surfactants, plasticizers, thickening polymers, and mixtures thereof.

18. The composition according to claim 1, which is in the form of a care or protection cream, a make-up product, foundation, lipstick, blusher, eyeshadow, mascara, eyeliner, nail varnish, or a formulation for "peel off" packs.

19. A method of treatment, comprising applying the composition according to claim 1 to the skin, the nails, the keratinous fibres, the semimucous membranes and/or the mucous membranes.

20. A method of treatment, comprising spreading the composition according to claim 1 to a part to be treated in a thickness allowing the formation of a film, leaving the composition in contact with the part for a sufficient period to obtain the desired effect and to allow the partial or complete drying of the composition and removing the film thus formed by peeling off at the end of the period.

21. A method of treatment, comprising applying the composition according to claim 9 to the skin, the nails, the keratinous fibres, the semimucous membranes and/or the mucous membranes.

22. A method of treatment, comprising spreading the composition according to claim 9 to a part to be treated in a thickness allowing the formation of a film, leaving the composition in contact with the part for a sufficient period to obtain the desired effect and to allow the partial or complete drying of the composition and removing the film thus formed by peeling off at the end of the period.

* * * * *

UNITED STATES PATENT AND TRADEMARK OFFICE
CERTIFICATE OF CORRECTION

PATENT NO.    : 6,287,552 B1
DATED         : September 11, 2001
INVENTOR(S)   : Tournilhac et al.

It is certified that error appears in the above-identified patent and that said Letters Patent is hereby corrected as shown below:

Column 8,
Line 41, "pentaerytlritol," should read -- pentaerythritol, --.

Signed and Sealed this

Twenty-sixth Day of March, 2002

Attest:

*Attesting Officer*

JAMES E. ROGAN
*Director of the United States Patent and Trademark Office*